(12) United States Patent
Sung et al.

(10) Patent No.: US 8,542,798 B2
(45) Date of Patent: Sep. 24, 2013

(54) BATTERY-TYPE X-RAY IMAGING APPARATUS

(75) Inventors: Ki-Bong Sung, Goyang-si (KR); Jong-Lae Park, Seoul (KR)

(73) Assignee: Poskom Co., Ltd., Paju-Si, Gyeonggi-Do (KR)

( * ) Notice: Subject to any disclaimer, the term of this patent is extended or adjusted under 35 U.S.C. 154(b) by 205 days.

(21) Appl. No.: 13/123,103

(22) PCT Filed: Oct. 6, 2009

(86) PCT No.: PCT/KR2009/005701
§ 371 (c)(1),
(2), (4) Date: Jun. 3, 2011

(87) PCT Pub. No.: WO2010/041859
PCT Pub. Date: Apr. 15, 2010

(65) Prior Publication Data
US 2011/0249800 A1    Oct. 13, 2011

(30) Foreign Application Priority Data

Oct. 7, 2008  (KR) .................. 10-2008-0098073

(51) Int. Cl.
*H05G 1/32* (2006.01)
*H05G 1/42* (2006.01)
*H05G 1/30* (2006.01)

(52) U.S. Cl.
USPC ........................... 378/103; 378/112; 378/114

(58) Field of Classification Search
USPC .................. 378/91, 101–105, 109–112, 114, 378/197, 198
See application file for complete search history.

(56) References Cited

U.S. PATENT DOCUMENTS 2,505,667 A * 4/1950 Futterman ..................... 315/205
2,576,934 A * 12/1951 Grier .............................. 315/76

(Continued)

FOREIGN PATENT DOCUMENTS

KR   100676217    1/2007
KR   1020080005000    1/2008

(Continued)

OTHER PUBLICATIONS

International Search Report mailed May 17, 2010 for PCT/KR2009/005701.

*Primary Examiner* — Anastasia Midkiff
(74) *Attorney, Agent, or Firm* — Lowe Hauptman & Ham, LLP (57) ABSTRACT

The present invention relates to an X-ray imaging apparatus, and more particularly, to an X-ray imaging apparatus in which a condenser is charged with low battery voltage, and the charged voltage of the condenser, or the sum voltage of the output voltage of the battery serially connected to the condenser and the charged voltage of the condenser is used as X-ray generating power. The X-ray imaging apparatus according to the present invention is configured such that the battery power and the condenser power are serially connected to provide power for operating the X-ray imaging apparatus, thus generating power for operating the X-ray imaging apparatus from the low battery power, and obtaining a lightweight and less bulky X-ray imaging apparatus. Further, the X-ray imaging apparatus according to the present invention senses the charged voltage of the condenser unit, and cuts off power being applied to the condenser charging unit from the battery when it is determined that the charging of the condenser unit is completed, thus reducing the power consumption of the battery.

6 Claims, 6 Drawing Sheets

(56) References Cited

U.S. PATENT DOCUMENTS

| | | | | |
|---|---|---|---|---|
| 2,589,720 | A | * | 3/1952 | McMath .................... 315/200 R |
| 2,659,854 | A | * | 11/1953 | Wengel ......................... 315/129 |
| 4,053,778 | A | * | 10/1977 | Franke ........................... 378/102 |
| 5,093,611 | A | * | 3/1992 | Nakamura et al. .............. 322/90 |
| 5,604,406 | A | * | 2/1997 | Gaus ............................... 315/56 |
| 7,522,704 | B2 | | 4/2009 | Sung et al. |
| 2008/0197711 | A1 | * | 8/2008 | Kato et al. .................... 307/104 |

FOREIGN PATENT DOCUMENTS

| | | |
|---|---|---|
| KR | 1020080053811 | 6/2008 |
| KR | 1020080084483 | 9/2008 |

* cited by examiner

BATTERY-TYPE X-RAY IMAGING APPARATUS

CROSS REFERENCE TO RELATED APPLICATION

This application claims the priority of Korean Patent Application No. 10-2008-0098073, filed on Oct. 7, 2008 in the KIPO (Korean Intellectual Property Office), the disclosure of which are incorporated herein in their entirety by reference. Further, this application is the National Phase application of International Application No. PCT/KR2009/005701, filed Oct. 6, 2009, which designates the United States and was published in Korea. Each of these applications is hereby incorporated by reference in their entirety into the present application.

TECHNICAL FIELD

The present invention relates to an X-ray imaging apparatus, and more particularly, to an X-ray imaging apparatus in which a condenser is charged with low battery voltage, and the charged voltage of the condenser, or the sum voltage of the output voltage of the battery serially connected to the condenser and the charged voltage of the condenser is used as X-ray generating power.

BACKGROUND ART

An X-ray imaging apparatus is a radiographic device which allows X-rays emitted by the collision of thermal electrons between a cathode and an anode to be transmitted through the body of a patient or an animal and develops the X-rays transmitted through the body of the patient or the animal on a film or a digital image panel to diagnose the health state of the patient or the animal. The X-ray imaging apparatus has been widely used as a device for simply and conveniently diagnosing the state of the fracture site of the patient or the animal, or whether the internal organs of the patient or the animal are abnormal without giving any pain to the patient or the animal. Recently, various techniques are developed to accurately photograph X-ray images of the patient or the animal in an easier-to-use manner.

Particularly, the X-ray imaging apparatus is manufactured in a mobile type so that the X-ray images of the patient or the animal can be photographed at a desired place anytime without being limited to place and time to directly diagnose the health state of the patient or the animal.

Figure 1:
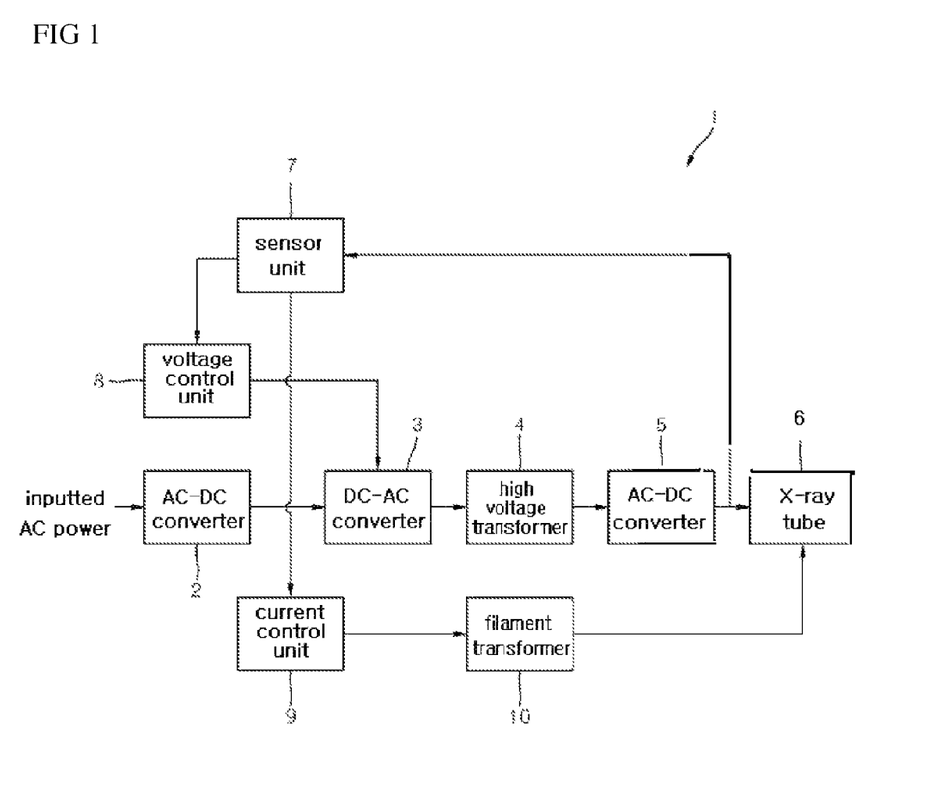
FIG. 1 is a functional block diagram illustrating a conventional mobile X-ray imaging apparatus using a commercial power supply according to the prior art.

FIG. 1 is a functional block diagram illustrating a conventional mobile X-ray imaging apparatus using a commercial power supply according to the prior art.

The conventional mobile X-ray imaging apparatus will be described hereinafter in more detail with reference to FIG. 1.

Referring to FIG. 1, the conventional mobile X-ray imaging apparatus 1 includes a AC-DC converting unit 2 for converting commercial AC power inputted thereto into DC power, a DC-AC converting unit 3 for converting the DC power converted by fast switching into high-frequency AC power ranging from 20 KHz to 300 KHz, a high-voltage transformer 4 for boosting the converted high-frequency AC power to high-voltage AC power, and an AC-DC converting unit 5 for converting the boosted high-voltage AC power into high-voltage DC power for application to an X-ray tube 6. The X-ray tube 6 is operated such that electric current is applied to a cathode filament installed in a high-vacuum glass bulb to generate heated thermal electrons, and the heated thermal electrons are accelerated and collide with an anode as a positive electrode made of a metal material such as tungsten to generate X-rays by a potential difference applied to the X-ray tube from the AC-DC converting unit 5.

A sensor unit 7 senses the magnitude of voltage applied to the X-ray tube 6 and the magnitude of current flowing through the filament of the X-ray tube 6 to generate a sensed signal for application to a voltage control unit 8 and a current control unit 9. The voltage control unit 8 produces a pulse signal to control the magnitude of voltage based on the sensed signal applied thereto from the sensor unit 7 and controls the switching on/off cycle of the DC-AC converting unit 3 based on the produced pulse signal to control the frequency of the AC power converted and generated from the AC power by the AC converting unit 3. In addition, the current control unit 9 controls the magnitude of current outputted from a filament transformer 10 based on the sensed signal applied thereto from the sensor unit 7 to ultimately control the magnitude of current flowing through the X-ray tube 7.

Figure 2:
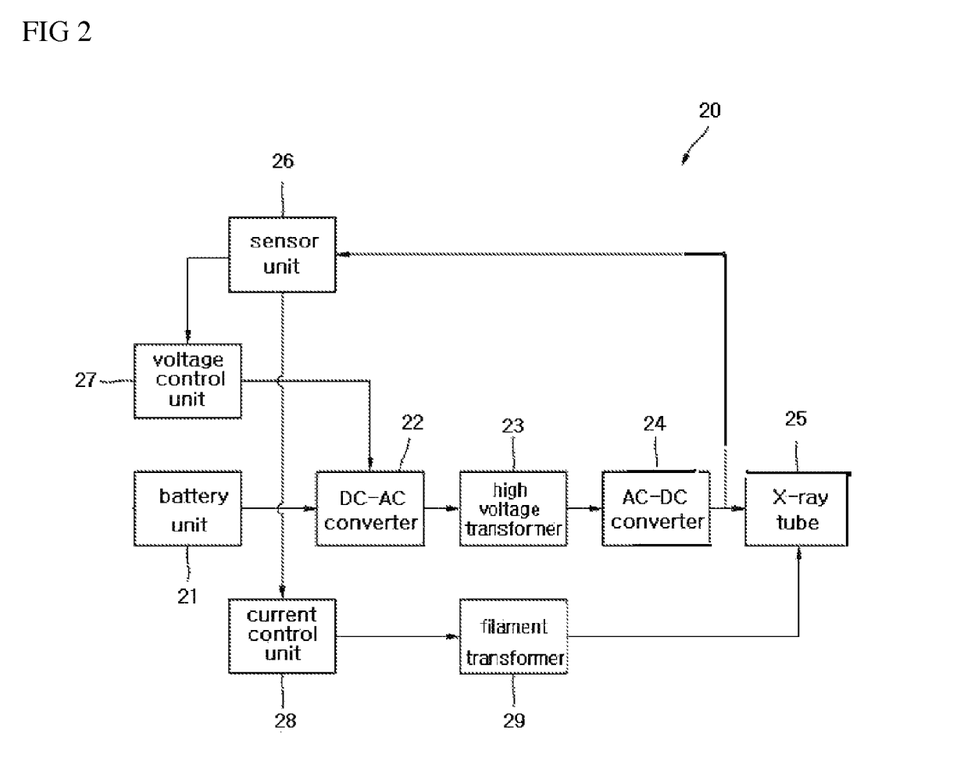
FIG. 2 is a functional block diagram illustrating a conventional mobile X-ray imaging apparatus 20 using a battery as a power supply according to the prior art.

FIG. 2 is a functional block diagram illustrating a conventional mobile X-ray imaging apparatus 20 using a battery as a power supply according to the prior art.

The conventional mobile X-ray imaging apparatus 20 will be described hereinafter in more detail with reference to FIG. 2.

Referring to FIG. 2, the conventional mobile X-ray imaging apparatus 20 includes a battery unit 21 consisting of a plurality of batteries serially connected to each other to output high-voltage DC power, a DC-AC converting unit 22 for converting the high-voltage DC power applied thereto from the battery unit 21 by fast switching into high-frequency AC power ranging from 20 KHz to 300 KHz, a high-voltage transformer 23 for boosting the converted high-frequency AC power to high-voltage AC power, an AC-DC converting unit 24 for converting the boosted high-voltage AC power into high-voltage DC power, and an X-ray tube 25 for generating X-rays using the high-voltage DC power applied thereto from the AC-DC converting unit 24.

The sensor unit 26, the voltage control unit 27, the current control unit 28, and the filament transformer 29 are operated in the same manner as that of the sensor unit 7, the voltage control unit 8, the current control unit 9, and the filament transformer 10 shown in FIG. 1 to control the magnitude of the DC voltage applied to the X-ray tube 25 and the magnitude of current applied to the filament of the X-ray tube 25.

DISCLOSURE OF INVENTION

Technical Problem

Since the conventional mobile X-ray imaging apparatus 1 using the commercial power supply as described above with reference to FIG. 1 uses a commercial AC power as an operating power supply, it must always be used at only a place where the commercial power supply is installed, or the commercial power supply must be brought from a place where commercial power supply is installed to a place where the mobile X-ray imaging apparatus is used through a long connection line so that commercial electric power can be applied to the mobile X-ray imaging apparatus 1, which causes an inconvenience to a user.

Meanwhile, the conventional mobile X-ray imaging apparatus 20 using the battery as described above with reference to FIG. 2 generates a high-voltage DC power using the battery only, and thus must include a plurality of batteries serially connected to each other. Therefore, since the conventional X-ray imaging apparatus 20 using the battery has an increased volume and weight, a user suffers from an inconvenience of having to carry the mobile X-ray imaging apparatus 20 in its practical use. In addition, since the conventional mobile X-ray imaging apparatus 20 must always charge the battery using the commercial power supply, in the case where it is required that the conventional mobile X-ray imaging apparatus 20 be used urgently, it is difficult to simply charge with low voltage of a charger for an automobile, a solar cell, or the like.

Typically, the X-ray imaging apparatus has characteristics in that its average power capacity is small but the instantaneous power capacity used during the X-ray photographing is increased greatly. Accordingly, the present invention is made to overcome the above-mentioned problems involved in the conventional X-ray imaging apparatus based on such characteristics of the X-ray imaging apparatus, and it is an object to provide an X-ray imaging apparatus which can generate high operating power with low battery power.

Another object of the present invention is to provide an X-ray imaging apparatus which uses lower battery power as an operating power, thereby leading to reduced weight and volume, and improved mobility.

Still another object of the present invention is to provide an X-ray imaging apparatus which can charge a battery even with low-voltage power of a charger for an automobile, a solar cell, or the like as well as a commercial power.

Technical Solution

To achieve the above objects, the present invention provides an X-ray imaging apparatus including: a condenser charging unit for receiving DC power having a first magnitude of a battery and generating DC power having a second magnitude; a condenser unit configured to be charged by the DC power having the second magnitude generated from the condenser charging unit; a control unit for sensing the magnitude of the charged power of the condenser unit and controlling the magnitude of power applied to the condenser charging unit from the battery unit; a high-voltage generating unit for generating high-voltage DC power using the charged power of the condenser unit; and an X-ray generating unit for generating X-rays using the high-voltage DC power generated from the high-voltage generating unit.

Preferably, the control unit includes a sensor unit for sensing the magnitude of the charged voltage of the condenser unit; a switching unit for interrupting the power applied to the condenser charging unit from the battery unit; and a charge control unit for controlling either the ON/OFF operation of the switching unit or the magnitude of the power supplied to the condenser unit through the condenser charging unit based on the sensed magnitude of the charged voltage of the condenser unit.

Preferably, the charge control unit controls the condenser unit to be charged with constant-current if the magnitude of the charged voltage of the condenser unit is less than a first threshold value, controls the ON/OFF operation of the switching unit to allow the condenser unit to be charged with current of a reduced magnitude if the magnitude of the charged voltage of the condenser unit is more than the first threshold value and is less than a second threshold value, and controls the switching unit to be turned off if the magnitude of the charged voltage of the condenser unit is more than the second threshold value.

Advantageous Effects

The X-ray imaging apparatus in accordance with the present invention has the following diverse advantageous effects as compared to a conventional mobile X-ray imaging apparatus.

First, the X-ray imaging apparatus in accordance with the present invention enables a battery power supply and a condenser power supply to be serially connected to each other to supply the operating power of the X-ray imaging apparatus so that high operating power of the X-ray imaging apparatus can be generated even with low battery power.

Second, the X-ray imaging apparatus in accordance with the present invention uses low battery power so that an X-ray imaging apparatus with a reduced weight and volume can be manufactured and a user can easily carry the X-ray imaging apparatus.

Third, the X-ray imaging apparatus in accordance with the present invention employs a condenser unit including a plurality of capacitors serially connected to each other so that when high operating voltage is needed, the X-ray imaging apparatus can be easily manufactured in a modified manner through a simple increase in the number of capacitors.

Fourth, the X-ray imaging apparatus in accordance with the present invention detects the charged voltage of the condenser unit so that it interrupts the power applied to the condenser charging unit from the battery unit if it is determined that the charging operation of the condenser unit is completed, thereby reducing the power consumption of the battery.

Fifth, the X-ray imaging apparatus in accordance with the present invention uses a battery of low power, and thus the battery can be charged even with low voltage of a charger for an automobile, a solar cell, or the like.

BEST MODE FOR CARRYING OUT THE INVENTION

An X-ray imaging apparatus according to the present invention will be described below in more detail with reference to the accompanying drawings.

Figure 3:
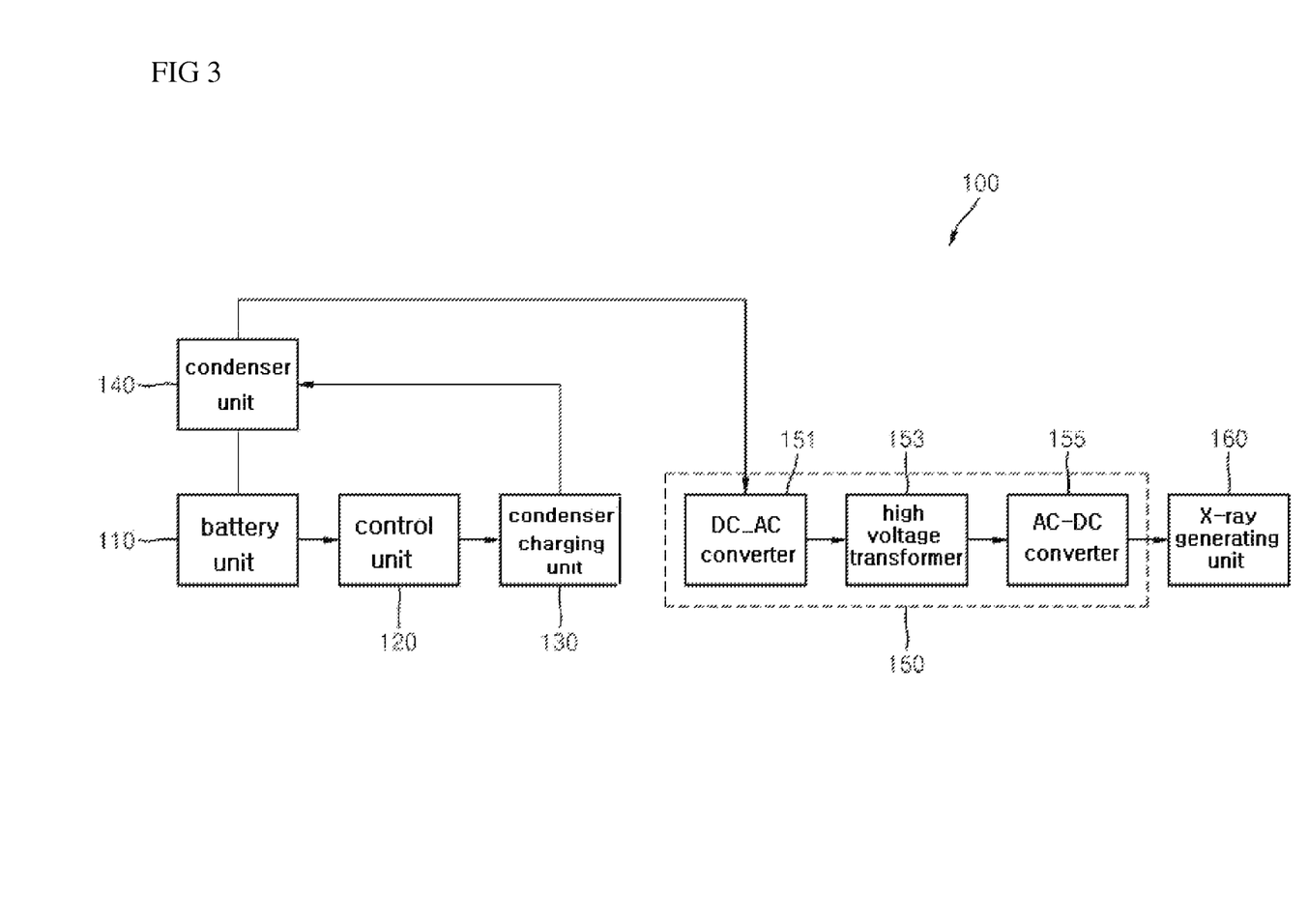
FIG. 3 is a functional block diagram illustrating an X-ray imaging apparatus according to one embodiment of the present invention.

FIG. 3 is a functional block diagram illustrating an X-ray imaging apparatus according to one embodiment of the present invention.

The X-ray imaging apparatus 100 will be described hereinafter in more detail with reference to FIG. 3.

Referring to FIG. 3, a battery unit 110 supplying low voltage, for example, power of 24V applies the output voltage to a condenser charging unit 130. The condenser charging unit 130 converts DC power having a first magnitude applied thereto from the battery unit 110 into DC power having a second magnitude for application to the condenser unit 140 under the control of the control unit 120. The condenser unit 140 is charged by the DC power having the second magnitude applied thereto from the condenser charging unit.

The operation of the condenser charging unit 130 converting the DC power having a first magnitude applied thereto from the battery unit 110 into the DC power having a second magnitude will be described hereinafter in more detail.

The DC power having a first magnitude applied to the condenser charging unit 130 from the battery unit 110 is switched with high frequency and is converted into AC power. The converted AC power is boosted to high voltage AC power, and the boosted AC power is converted into DC power having a second magnitude through a rectifier. One example of the condenser charging unit 130 according to the present invention includes a DC-AC converter for converting the DC power having a first magnitude applied thereto from the battery unit 110 into AC power, and a transformer for boosting the converted AC power, and a rectifier for rectifying the boosted AC power to generate the DC power having a second magnitude. The AC power applied to a primary coil of the transformer is strayed with AC power boosted in a secondary coil. The primary coil and the secondary coil of the transformer are electrically isolated from each other.

Figure 5:
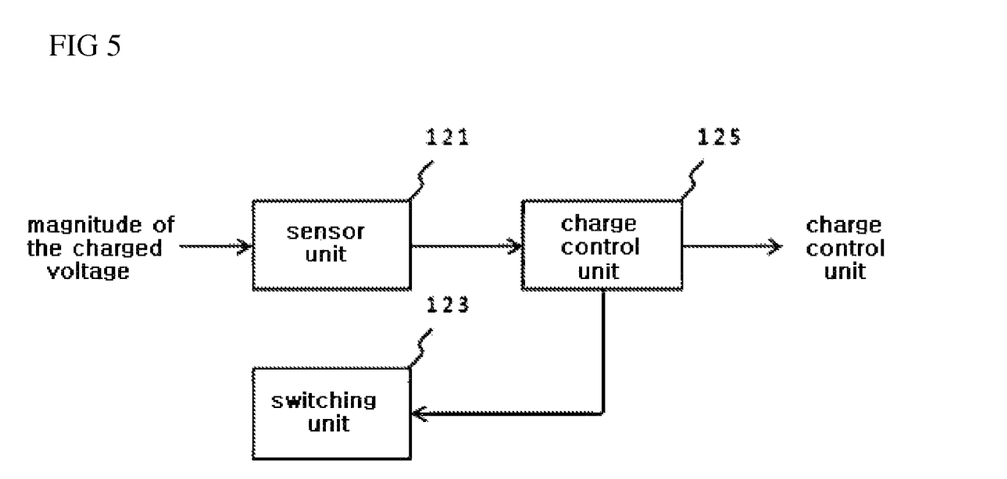
FIG. 5 is a functional block diagram illustrating one example of a control unit according to the present invention.

The control unit 120 interposed between the battery unit 110 and the condenser charging unit 130 to control the power applied to the condenser charging unit 130 from the battery unit 110 will be described hereinafter in more detail with reference to FIG. 5.

The control unit 120 includes a sensor unit 121 for sensing the magnitude of the voltage of the condenser unit 140, which is charged through the condenser charging unit 130, a switching unit 123 for interrupting the power applied to the condenser charging unit 130 from the battery unit 110, and a charge control unit 125 for controlling either the ON/OFF operation of the switching unit 123 or the magnitude of the power supplied to the condenser unit 140 through the condenser charging unit 130 based on the sensed magnitude of the charged voltage of the condenser unit 140. Preferably, the charge control unit 125 controls the magnitude of the DC power generated from the condenser charging unit 130 so that the condenser unit 140 is charged by a constant-voltage/constant-current charging method.

Figure 6:
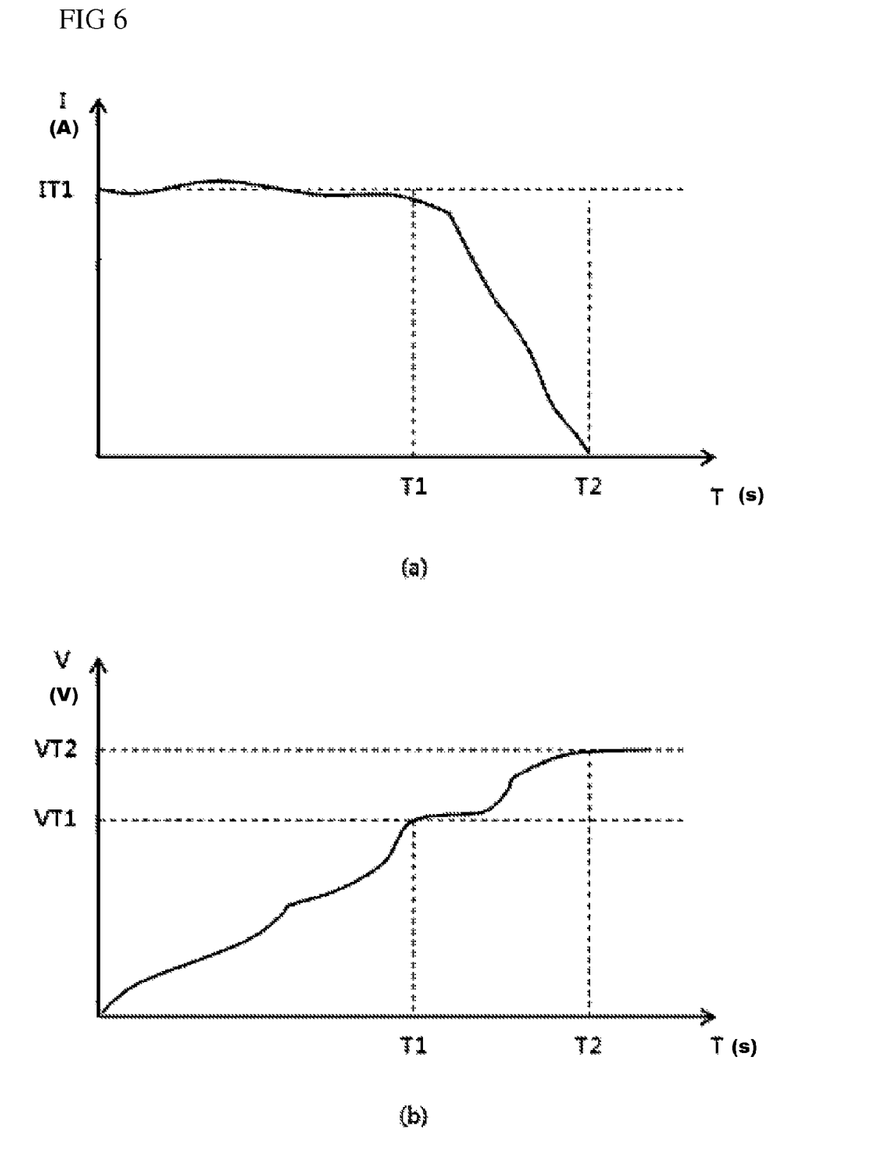
FIG. 6 is a waveform chart illustrating one example of the charged voltage and the charged current of the condenser unit according to the present invention.

One example of the control operation of the charge control unit 125 will be described hereinafter with reference to FIG. 6.

The charge control unit 125 controls the switching unit to be turned on, and simultaneously converts the battery power having a first magnitude applied to the condenser charging unit 130 into a current value IT1 of a predetermined magnitude to control the condenser unit 140 to be charged with constant-current. The charge control unit 125 continues to sense the magnitude of the charged voltage of the condenser unit 140 through the sensor unit 121, and controls the magnitude of the charged current applied to the condenser unit 140 to be reduced at a time point when the magnitude of the charged voltage of the condenser unit 140 exceeds a first threshold value VT1 based on the sensed magnitude of the charged voltage of the condenser unit 140. The charge control unit 125 reduces the time during which the switch is turned on, and extends the time during which the switch is turned off or reduces the magnitude of the power generated from the condenser charging unit 130 in order to reduce the magnitude of the charged current applied to the condenser unit 140. The control unit 125 generates a pulse control signal corresponding to the turn-on/off time of the switching unit 123 so as to control the turn-on/off time of the switching unit 123, and controls the switching unit 123 to be turned on/off in response to the generated pulse control signal.

In the meantime, the charge control unit 125 controls the switching unit 123 to be turned off to interrupt the supply of the power of the battery unit 110 to prevent the power of the battery 110 from being continuously applied to the condenser charging unit 130 at a time point T2 when the magnitude of the charged voltage of the condenser unit 140 sensed through the sensor unit 121 reaches a second threshold value VT2. Preferably, the second threshold value VT2 is a target charged voltage of the condenser unit 140. The charge control unit 125 continues to sense the magnitude of the charged voltage of the condenser unit 140, and resumes the charging of the condenser unit 140 when the magnitude of the charged voltage of the condenser unit 140 is less than the first threshold value or the second threshold value due to discharge of the condenser unit 140.

Another example of the control operation of the charge control unit 125 will be described hereinafter.

The charge control unit 125 continues to sense the magnitude of the charged voltage of the condenser unit 140 through the sensor unit 121. Then, the charge control unit 125 controls the switching unit 123 to be turned on and simultaneously converts the battery power having a first magnitude applied to the condenser charging unit 130 into a current value IT1 of a predetermined magnitude to control the condenser unit 140 to be charged with constant-current until the magnitude of the charged voltage of the condenser unit 140 reaches the second threshold value VT2 based on the sensed magnitude of the charged voltage of the condenser unit 140. On the other hand, if the magnitude of the charged voltage of the condenser unit 140 exceeds the second threshold value VT2, the charge control unit 125 controls the switching unit 123 to be turned off to prevent the power of the battery unit 110 from being continuously applied to the condenser charging unit 130. The charge control unit 125 continues to sense the magnitude of the charged voltage of the condenser unit 140, and resumes the charging of the condenser unit 140 when the magnitude of the charged voltage of the condenser unit 140 is less than the second threshold value due to discharge of the condenser unit 140.

The condenser unit 140 includes a plurality of high-capacity capacitors which are serially connected to each other, and the condenser unit 140 and the battery unit 110 are serially connected to each other. Thus, the magnitude of the charged voltage of the condenser unit 140 and the magnitude of the output voltage of the battery unit 110 are summed up so that the voltage of the summed magnitudes is supplied to the high-voltage generating unit 150.

The high-voltage generating unit 150 includes a DC-AC converting unit 151, a high-voltage transformer 153, and an AC-DC converting unit 155.

The DC-AC converting unit 151 converts the DC power inputted by fast switching into high-frequency AC power, and the high-voltage transformer 153 boosts the converted high-frequency AC power to high-voltage AC power to increase the magnitude of the voltage. The AC-DC converting unit 155 converts the boosted high-voltage AC power into high-voltage DC power for application to the X-ray tube 160, which in turn generates X-rays using the DC power.

Figure 4:
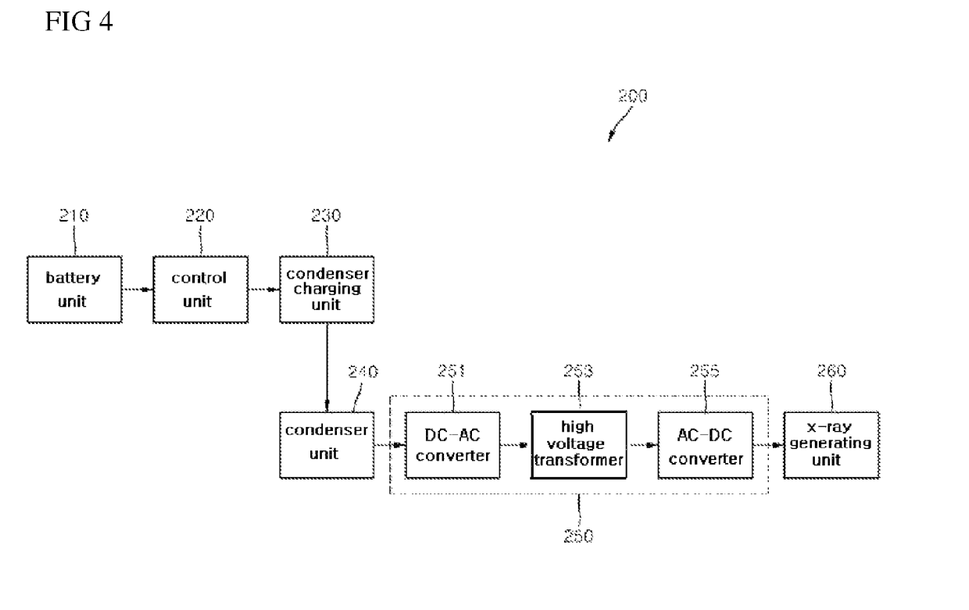
FIG. 4 is a functional block diagram illustrating an X-ray imaging apparatus according to another embodiment of the present invention.

FIG. 4 is a functional block diagram illustrating an X-ray imaging apparatus according to another embodiment of the present invention.

The X-ray imaging apparatus 200 will be described hereinafter in more detail with reference to FIG. 4.

Referring to FIG. 4, a condenser charging unit 230 converts DC power having a first magnitude applied thereto from a battery unit 210 into DC power having a second magnitude for application to a condenser unit 240 to charge the condenser unit 240 under the control of a control unit 220. The control unit 220 is interposed between the battery unit 210 and the condenser charging unit 230, and senses the magnitude of the charged voltage of the condenser unit 240 to control the magnitude of the power applied to the condenser charging unit 230 from the battery unit 210.

The condenser unit 240 includes a plurality of high-capacity capacitors which are serially connected to each other, and supplies the charged voltage thereof to a voltage generating unit 250. The voltage generating unit 250 includes a DC-AC converting unit 251, a high-voltage transformer 253, and an AC-DC converting unit 255. The high-voltage generating unit 250 amplifies the DC power applied thereto from the condenser unit 240 to generate high-voltage DC power. An X-ray tube 260 generates X-rays using the DC power applied thereto from the high-voltage generating unit 250.

In another embodiment of the present invention shown in FIG. 4, the high-voltage generating unit 250 is different from the high-voltage generating unit 150 according to one embodiment of the present invention shown in FIG. 3 in that it uses only the charged voltage of the condenser unit 240. Besides, the elements constituting the X-ray imaging apparatus of FIG. 4 are operated in the same manner as that of the elements constituting the X-ray imaging apparatus of FIG. 3. Thus, the elements 210, 220, 230, 240, 250 and 260 constituting the X-ray imaging apparatus according to another embodiment shown in FIG. 4 can be described with reference to the elements 110, 120, 130, 140, 150 and 160 constituting the X-ray imaging apparatus according to one embodiment of the present invention shown in FIG. 3.

While the present invention has been described in connection with the exemplary embodiments illustrated in the drawings, they are merely illustrative, and the invention is not limited to these embodiments. It is to be understood that various equivalent modifications and variations of the embodiments can be made by a person having an ordinary skill in the art without departing from the spirit and scope of the present invention. Therefore, the true technical scope of the present invention should be defined by the technical spirit of the appended claims.

INDUSTRIAL APPLICABILITY

The battery-type X-ray imaging apparatus according to the present invention has a merit in that since the X-ray imaging apparatus can be manufactured in a small size, it is easy to carry and convenient to use. Therefore, the inventive battery-type X-ray imaging apparatus can be used for diagnosis of the human and animals in a variety of medical fields in place of a conventional solid or mobile X-ray imaging apparatus.

The invention claimed is:

1. An X-ray imaging apparatus comprising:
   a condenser charging unit for receiving DC power having a first magnitude of a battery unit and generating DC power having a second magnitude;
   a condenser unit configured to be charged by the DC power having the second magnitude generated from the condenser charging unit;
   a control unit for sensing the magnitude of the charged power of the condenser unit and controlling the magnitude of power applied to the condenser charging unit from the battery unit;
   a high-voltage generating unit for generating high-voltage DC power using the charged power of the condenser unit; and
   an X-ray generating unit for generating X-rays using the high-voltage DC power generated from the high-voltage generating unit,
   wherein
   the high-voltage generating unit is configured to receive the DC power of the battery unit and the condenser unit which are serially connected to each other and to generate high-voltage DC power using the DC power of the battery unit and the condenser unit.

2. The X-ray imaging apparatus according to claim 1, wherein the control unit comprises:
   a sensor unit for sensing the magnitude of the charged voltage of the condenser unit;
   a switching unit for interrupting the power applied to the condenser charging unit from the battery unit; and
   a charge control unit for controlling either the ON/OFF operation of the switching unit or the magnitude of the power supplied to the condenser unit through the condenser charging unit based on the sensed magnitude of the charged voltage of the condenser unit.

3. The X-ray imaging apparatus according to claim 2, wherein the charge control unit controls
   the condenser unit to be charged with constant-current if the magnitude of the charged voltage of the condenser unit is less than a first threshold value,
   controls the ON/OFF operation of the switching unit to allow the condenser unit to be charged with current of a reduced magnitude if the magnitude of the charged voltage of the condenser unit is more than the first threshold value and is less than a second threshold value, and
   controls the switching unit to be turned off if the magnitude of the charged voltage of the condenser unit is more than the second threshold value.

4. The X-ray imaging apparatus according to claim 3, wherein the condenser unit is charged by a constant-voltage/constant-current charging method.

5. The X-ray imaging apparatus according to claim 2, wherein the condenser unit comprises a plurality of capacitors serially connected to each other.

6. The X-ray imaging apparatus according to claim 1, wherein the condenser charging unit comprises:
   a DC-AC converter for converting the DC power having the first magnitude of the battery unit into AC power;
   a transformer for boosting the converted AC power; and
   a rectifier for rectifying the boosted AC power to generate the DC power having the second magnitude.

* * * * *